United States Patent [19]

Hartley, Sr.

[11] Patent Number: 4,620,536
[45] Date of Patent: Nov. 4, 1986

[54] MODULAR TRAY ASSEMBLY FOR A RESPIRATORY APPARATUS

[75] Inventor: Alvin W. Hartley, Sr., Atlanta, Ga.

[73] Assignee: Gunning Medical Products, Inc., Atlanta, Ga.

[21] Appl. No.: 735,177

[22] Filed: May 17, 1985

[51] Int. Cl.[4] .................................................. A62B 7/00
[52] U.S. Cl. ............................. 128/200.24; 128/202.13
[58] Field of Search ..................... 128/200.21, 200.24, 128/202.13, 204.18, 205.25

[56] References Cited

U.S. PATENT DOCUMENTS 2,449,165 9/1948 Heidbrink ..................... 128/200.13

Primary Examiner—Stephen F. Husar
Attorney, Agent, or Firm—Newton, Hopkins & Ormsby

[57] ABSTRACT

A modular tray assembly including a first modular tray member having side wall members, a top wall member, and a bottom wall member. Secured to at least two side wall members are block bracket members that are used to support adjacent modular tray members having side, bottom, and top wall members. Each of the side wall members of the adjacent modular tray members has a channel bracket support member that engages the associated corresponding block bracket member of the first modular tray member. The bottom wall member of the first modular tray member has a planar support bracket member vertically extending therefrom which has a bracket member having a cylindrical opening at the distal end thereof. A cylindrical support member is received through the cylindrical opening and also by a circular opening in a bracket member secured to one of the side wall members of the first modular tray member for supporting the tray assembly. The cylindrical support member is mounted on a base support which has wheels for transporting the tray assembly from place to place. Respiratory apparatus is mounted on the top portion of the cylindrical support member.

8 Claims, 2 Drawing Figures

MODULAR TRAY ASSEMBLY FOR A RESPIRATORY APPARATUS

BACKGROUND OF THE INVENTION

1. Field of the Invention

The invention relates to tray apparatus and, in particular, tray apparatus on a mobile support pedestal for the treatment of respiratory patients.

2. Description of the Prior Art

In the treatment of respiratory patients it is necessary to provide for the storage of medication and medical supplies that are used in the care and treatment of the patient, either in a hospital or at home. It has been found that a major cost of the treatment is attributed to increased spending due to the inefficient handling of medication and unnecessary waste of medication materials and equipment associated with the treatment of the respiratory patient. It is desirable to consolidate as much as possible into a confined area the equipment and medication used on a daily basis in the treatment of the respiratory illness. At the same time proper aseptic procedures must be followed. In this way the quality of patient care and the standard of care is vastly improved with a higher utilization of services. As a result, it is possible to more accurately monitor and control the cost in the treatment of respiratory patients.

BRIEF DESCRIPTION OF THE INVENTION

One aspect of the present invention is the design and arrangement of modular tray members in an assembly which conserves space and preserves aseptic procedures. A first modular tray member is centrally disposed and includes contiguous wall members, including side wall members and a bottom wall member. The bottom wall member is connected to a first support bracket member that includes a planar support member extending vertically and a bracket member at the distal end thereof. At least two of the side walls members have tapered block bracket members fixed thereto for connecting a plurality of modulular tray members for storage. Each of the modular members has a channel shaped support member complementary to the block bracket members to enable supporting the additional storage modular tray members from the first modular tray member. The first modular tray is supported by a support member connected to the first support bracket member and an additonal bracket member extending from a side wall member.

The first modular tray member is used for storing medication in vials, and tongue depressors, cotton tipped applicators, syringes, laryngoscopes and blades, nipples and nuts and saline solution. Two additional storage modules connected to the centrally disposed first modular tray member are used for equipment such as manifold nebulizer systems, oxygen tubing, face mask, humidifier bottles, suction catheter, sterile water. Alternatively one of these storage modules can be used for syringes or as a container for tracheostomy tube, inner cannula and obturator sermerge in normal saline solutions. Each of the modular tray members has a hinged top cover for approriate aseptic procedures. In similar fashion, a fourth modular tray member is connected to the first modular tray member by similar block bracket and channel shaped support member complementary in shape to the block bracket. The fourth modular tray member is used for attaching a clipboard for holding documents and record data used during the treatment of the patient.

A second aspect of the invention is the configuration of the modular tray members and the manner of supporting them on a mobile support base. The first support bracket member extending from the bottom wall member of the first modular tray member includes a bracket member at the distal end that has a tubular opening formed therein. Also a bracket member with a curved opening is secured to one of the side wall members of the first modular tray member. The tubular opening and curved opening are vertically aligned to receive a cylindrical support member. The cylindrical support member is engaged by the bracket members to support the tray assembly.

The cylindrical support member is mounted on a base which has a plurality of wheels for the purpose of facilitating movement of the tray members from one place to another. The upper portion of the cylindrical support member is used for supporting respiratory equipment used for treating the patient.

The modular tray apparatus according to the invention may be used in hospitals, emergency rooms, patient rooms, isolation areas, intensive care units, emergency medical clinics, doctors' offices, dentists' offices, diagnositic centers, respiratory care service centers and for home care.

DETAILED DESCRIPTION OF THE PREFERRED EMBODIMENT

Figure 1:
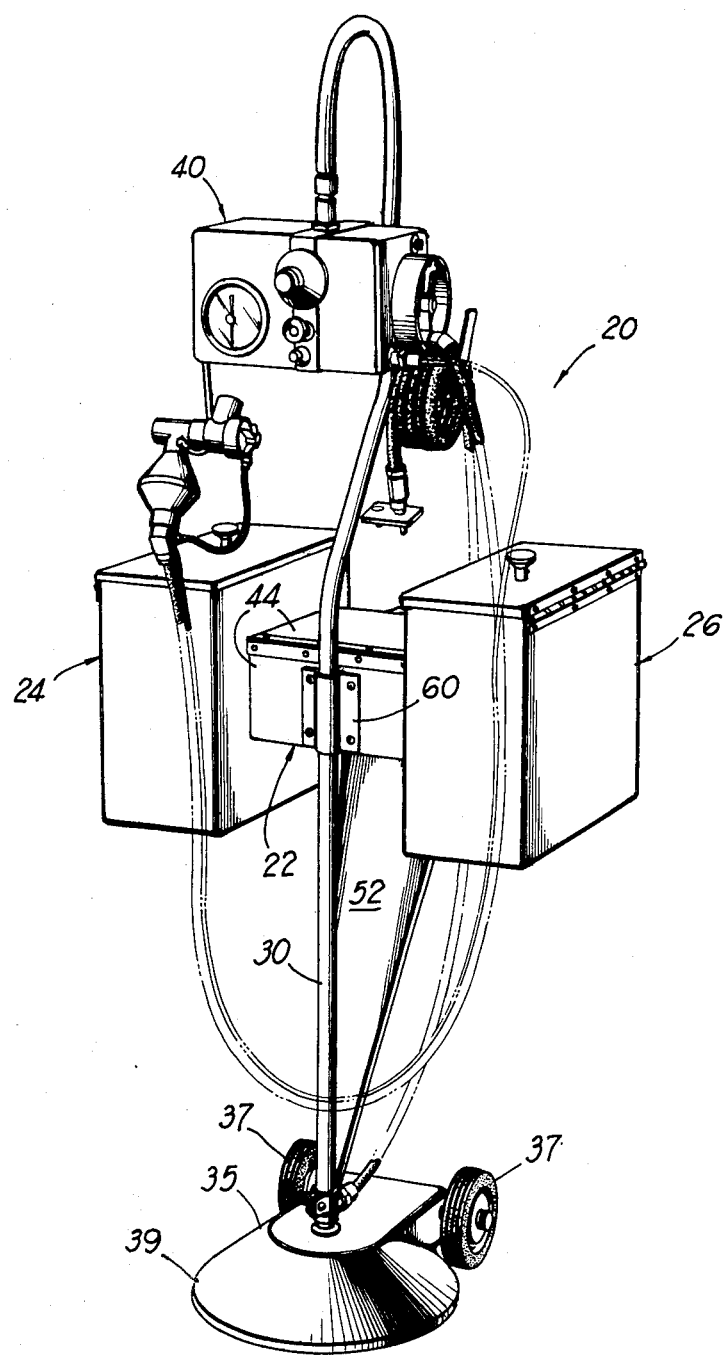
FIG. 1 is a perspective view of the modular tray apparatus according to the present invention mounted on a mobile support.

Referring now to FIG. 1, there is shown a modular tray assembly according to the present invention mounted on the pedestal that is used for a portable respiratory unit or the like. The tray assembly generally designated 20 includes a modular tray member 22 for medication that is disposed centrally within the assembly. On each side of the module 22 are modular tray members 24 and 26 for storage of supplies. The tray assembly is supported by a cylindrical support member 30 which is mounted on a base member 35 having a pair of wheels 37 for portable transport of the tray assembly from one place to another. The base support member includes a funnel shaped stand member 39 which provides a stable support to the tray assembly. At the upper portion of the cylindrical support member 30 is a respiratory apparatus 40 which includes components that are well known in the respiratory technology field and do not form a part of the present invention.

Figure 2:
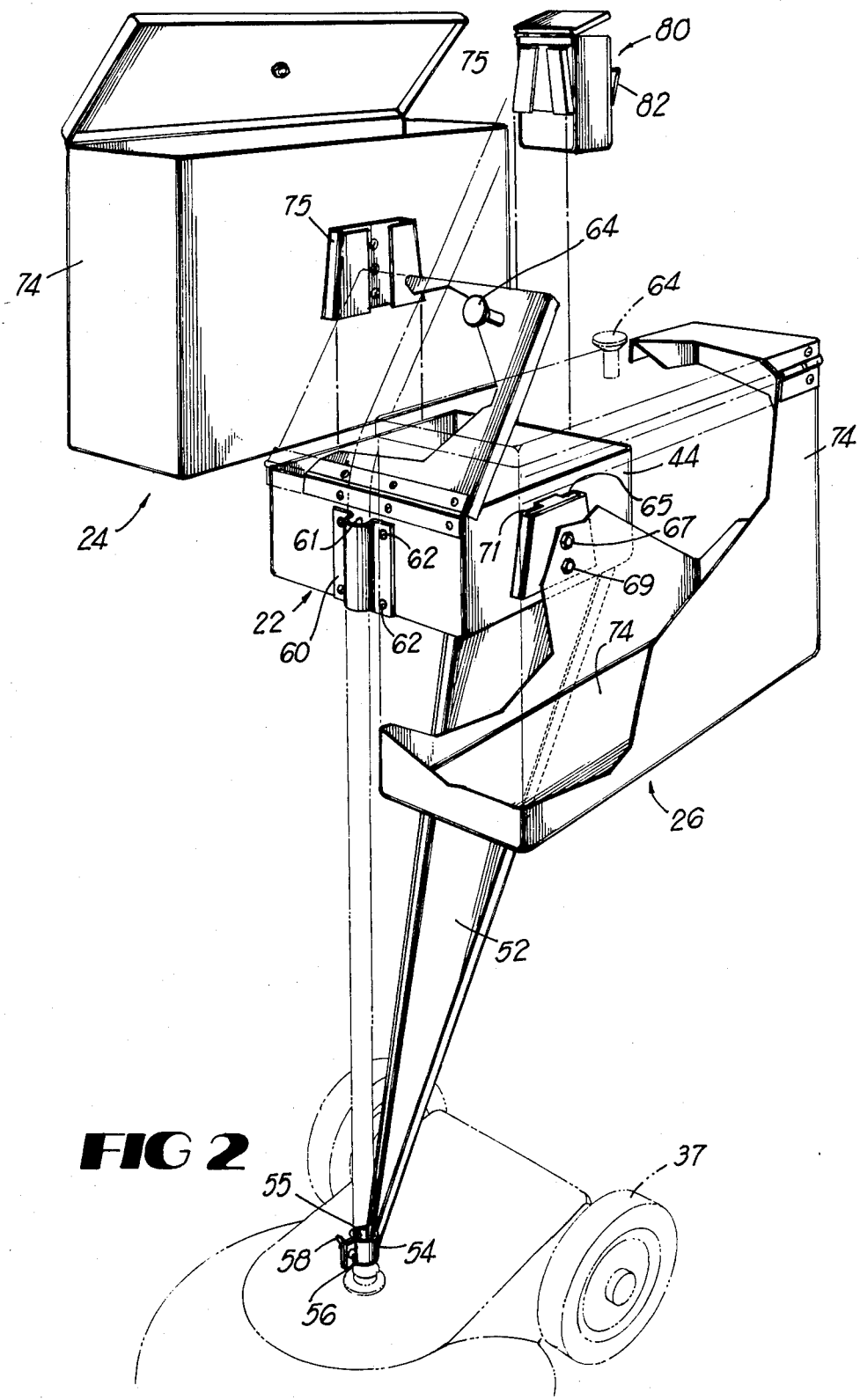
FIG. 2 is an exploded perspective view of the modular tray apparatus with certain parts in section to show certain details thereof.

Referring now to FIG. 2, there is shown details of the tray assembly which can be attached to the mobile pedestal as shown in FIG. 1 or to a wall or any other suitable respiratory equipment. Modular tray member 22 has a plurality of contiguous wall members 44 on the sides, bottom and top thereof. Extending from the bottom wall member is a support bracket member 52 that extends perpendicularly in a vertical plane. At the distal end of the support bracket member 52 is a bracket member 54 which is formed with a tubular opening 55 for engaging the cylindrical member 30. Engagement of the member 30 is facilitated by a screw member 56 and a wing nut 58. Aligned with the bracket member 54 is a bracket member 60 that is formed with a curved opening 61. Bracket member 60 is secured to a side wall member 24 screws 62. By this structure the modular tray 22 is securely supported by the cylindrical support member 30, and base member 35 and stand member 39. The top wall member 44 is hinged to one of the side wall members for opening and closing the top wall member by use of the knob 64 to ensure aseptic procedures.

The remaining side wall members 24 of the modular tray member 22 have a block bracket member 65 secured on the outside surface thereof by nuts and bolts 67 and 69. Side portions of the block bracket members 65 are tapered. Each of the storage modules 24 and 26 have contiguous wall members 74 which include side walls, a bottom wall and a top wall. Similar to tray member the top wall is secured to one of the side walls by a hinge member for aseptic purposes. On one of the side wall members 74 is a channel shaped support member 75 which complementary in shape to the block bracket members 65 on modular tray member 22. By this structure the modular tray assemblies 24 and 26 are slidably supported from the modular tray member 22 by insertion of the support member 75 over a corresponding block bracket member 65.

In similar fashion a third side wall member 24 of the modular tray 22 has a block bracket member 65 that is used for supporting a third modular tray member 80 that has a channel shaped support bracket 75 fixed thereto. Also secured to modular tray member 80 is a clipboard 82 for holding document or record information of a patient.

Modular tray member 22 is used as a medication module and is capable of storing a plurality of vials of medication as well as a storage space for tongue depressors, cotton tipped applicators, syringes, laryngoscopes and blades, nipples and nuts and units of normal saline solution that are typically used in the treatment of patients experiencing respiratory problems.

Modular trays 24 and 26 are used for the storage of pieces of equipment, such as, manifold nebulizer systems, oxygen tubing, face mask, humidifier bottle, suction catheter and sterile water. If desired, one of the modulular trays 24 and 26 can be used for the storage of clean equipment while the other may be used for the storage of discarded equipment.

Modular tray member 80 is used as a contaminating module for the use of syringes or as a container for tracheostomy to enter cannula and obturator sermerge in normal saline solutions. Also disposed on module tray member 80 is a data clipboard 80 for retaining all pertinent information in the treatment of the patient including records, changes and memos.

By the above described invention there is described a modular tray assembly that is beneficial in the field of respiratory technology. This tray assembly may be used for the storage of equipment and medication that is used constantly during the treatment of the patient whether it is in a clinical practice location or at home. The tray assembly modules can be positioned on a pedestal for fast mobility or attached to a respirator or mounted on a wall in a patient's room. Thus the versatility of the tray assembly is such that it can be used in general hospitals, emergency rooms, patient rooms, isolation areas, intensive care units, emergency medical clinics, doctors' offices, dentists' offices, diagnostic centers, respiratory care services, home care and any other suitable institution where medical treatments are rendered to in- and out-patients.

It will be obvious to those skilled in the art that many variations may be made in the embodiments here chosen for the purpose of illustrating the present invention and full result may be had to the doctrine of equivalents without departing from the scope of the present invention as defined by the appended claims.

What is claimed is:

1. Tray assembly for respiratory apparatus or the like comprising
   first modular tray means having a plurality of side wall members and a bottom wall member;
   first bracket means having a planar support member extending in a vertical plane from said bottom wall member and having a first bracket member disposed at the distal end of said planar support member;
   second bracket means connected to at least two of said wall members, said second bracket means having a tapered block shape,
   third bracket means connected to one of said side wall members;
   second and third modular tray means each having bracket support means secured thereto, said bracket support means having a channel shape complementary to said second bracket means for supporting said second and third modular tray means on opposing side wall members of said first modular tray means; and
   support means extending between said first and third bracket means to support said modular tray means.

2. Apparatus according to claim 1 wherein said second bracket means is connected to a third one of said side wall members for supporting a fourth modular tray means having a channel shaped bracket support means.

3. Apparatus according to claim 1 wherein said first bracket member includes a tubular opening for receiving a cylindrical support member.

4. Apparatus according to claim 3 wherein said third bracket means has a curved opening in vertical alignment with the tubular opening for receiving said cylindrical support member.

5. Apparatus according to claim 4 wherein said cylindrical support member is mounted on a support base having wheels.

6. Apparatus according to claim 5 wherein the upper portion of said cylindrical support member is connected to respiratory medical means.

7. Apparatus according to claim 1 wherein each of said modular tray means includes a top cover hinged thereto.

8. Apparatus according to claim 2 wherein said fourth modular tray means has a clip member attached thereto for holding document material.

* * * * *